United States Patent
Borzatta et al.

(10) Patent No.: US 7,402,709 B2
(45) Date of Patent: Jul. 22, 2008

(54) PROCESS FOR SYNTHESIZING HELIOTROPINE AND ITS DERIVATIVES

(75) Inventors: Valerio Borzatta, Bologna (IT); Elisa Capparella, Ravenna (IT); Carlotta Gobbi, Ravenna (IT); Elisa Poluzzi, Calderara di Reno (IT)

(73) Assignee: Endura S.p.A., Bolonga (IT)

( * ) Notice: Subject to any disclaimer, the term of this patent is extended or adjusted under 35 U.S.C. 154(b) by 86 days.

(21) Appl. No.: 10/577,846

(22) PCT Filed: Oct. 28, 2004

(86) PCT No.: PCT/EP2004/052710

§ 371 (c)(1), (2), (4) Date: Apr. 27, 2006

(87) PCT Pub. No.: WO2005/042512

PCT Pub. Date: May 12, 2005

(65) Prior Publication Data

US 2007/0100167 A1    May 3, 2007

(30) Foreign Application Priority Data

Oct. 30, 2003   (IT)   ................. MI2003A2103

(51) Int. Cl.
*C07C 45/90* (2006.01)
(52) U.S. Cl. ................... 568/432; 568/437
(58) Field of Classification Search ........... 568/432, 568/437

See application file for complete search history.

(56) References Cited

U.S. PATENT DOCUMENTS 5,095,128 A * 3/1992 Sidot et al. ................. 549/436

FOREIGN PATENT DOCUMENTS

JP   55022615   2/1980
JP   57009734   1/1982

OTHER PUBLICATIONS

Quelet et al., "Synthesis of Anisic Alcohol", *Database Caplus, Chemical Abstracts Service*, No. 1937:817 Columbus, Ohio (1937).

Futami et al., "Reactions of Alkylarenes, Benzyl Alcohols, Sulfides, and Phosphine with Manganese (III) Acetate-Chloride Ions", *Bulletin of the Chemical Society of Japan*, vol. 62, No. 11, pp. 3567-3571 (1989).

* cited by examiner

*Primary Examiner*—Sikarl A Witherspoon
(74) *Attorney, Agent, or Firm*—Abelman, Frayne & Schwab

(57) ABSTRACT

A new high-yield, easily industrialized process for synthesizing compounds of formula (IV), in which $X_1$ and $X_2$, the same or different, are linear or branched C1-C8 alkyls, n and m are 0, 1 or 2, with the proviso that n and m are not simultaneously 0; or $(OX_1)n$ and $(OX_2)m$ taken together form an O-T-O group where T is chosen from $—CH_2—$, $—CH_2CH_2$, $—CH_2CH_2CH_2—$, $—C(CH_3)_2—$. The process comprises treating a chloromethyl derivative (I) with an alkaline acetate to form the intermediate acetylderivative (II); the intermediate (II) is to hydrolysed to form the alcohol (III); the alcohol (III) is then oxidised in the presence of air and catalysts to obtain the desired derivative (IV). The process runs its course within a short period of time, with high yields and high selectivity; in addition, the process does not require purification and separation of the intermediates and can therefore be favourably conducted in a single batch.

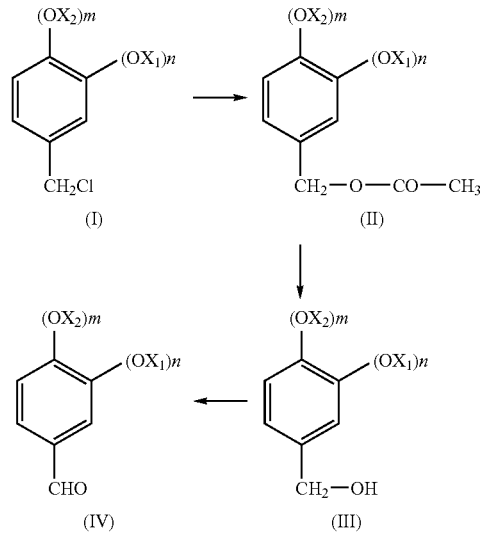

9 Claims, No Drawings

PROCESS FOR SYNTHESIZING HELIOTROPINE AND ITS DERIVATIVES

FIELD OF THE INVENTION

The present invention relates to the synthesis of aldehyde derivatives of benzodioxoles or dihydrobenzenes.

PRIOR ART 3,4-methylenedioxy benzaldehyde (also known as heliotropine or piperonal) is a compound contained in tropical and subtropical plant etheric oils. It is principally used in the fragrance industry and for the production of perfumes.

Many heliotropine synthesis pathways are known. Some of the synthesis pathways start from 1,2 methylenedioxybenzene. For example, it is known to treat this compound with gaseous HCl, ZnCl and formaldehyde in benzene, forming piperonyl chloride; piperonyl chloride is then made to react with a hexamine in alcohol (Sommelet reaction) and then hydrolysed, thus obtaining heliotropine. The reaction of 1,2 methylenedioxybenzene with formaldehyde, HCl and m-nitrobenzenesulfonic acid, and an aluminium catalyst, to obtain heliotropine is also known. Other authors (GB 1,591,268) propose a transformylation process (Vilsmeier-Haack reaction), in which 1,2 methylenedioxybenzene, treated with N-alkylformanilide and phophorus oxychloride, is converted to heliotropine. All these processes are not entirely satisfactory in that they are considerably non-specific, and/or require intermediate purification passages or give insufficient yields.

In other processes 1,2 methylenedioxybenzene is treated with glyoxylic acid and alkali: the 3,4 methylenedioxymandelic acid thus obtained is converted into heliotropine by oxidative decarboxylation, achieved with $HNO_3$ and HCl (U.S. Pat. No. 5,095,128) or with phosphoric acid (DE 2,754,490).

Currently, there is a lack of production processes starting from 1,2 methylenedioxybenzene or its derivatives, which have high specificity, excellent yields and avoid the need for intermediate purifications. The present invention is a response to this need.

SUMMARY

The present invention provides a process for obtaining a compound of formula (IV)

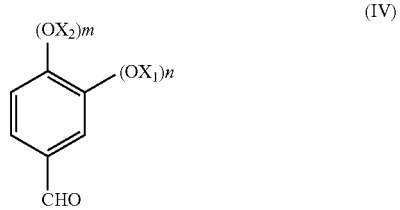

in which $X_1$ and $X_2$, the same or different, are linear or branched C1-C8 alkyls, n and m are 0, 1 or 2, with the proviso that n and m are not simultaneously 0; or $(OX_1)n$ and $(OX_2)m$ taken together form an —O-T-O— group where T is chosen from —$CH_2$—, —$CH_2CH_2$—, —$CH_2CH_2CH_2$—, —$C(CH_3)_2$—, said process comprising the following passages:

(i) treating a chloromethyl derivative of formula (I) with an alkaline acetate to form the acetyl derivative of formula (II), where in formulae (I) and (II) $X_1$, $X_2$, m and n have the aforesaid meanings;

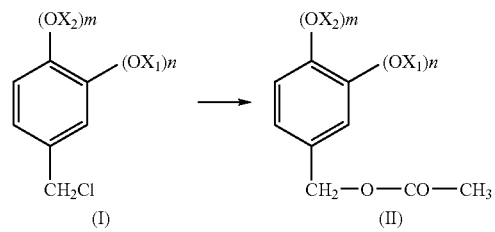

(ii) hydrolyzing compound (II) to form the alcohol (III), where $X_1$, $X_2$, m and n have the aforesaid meanings;

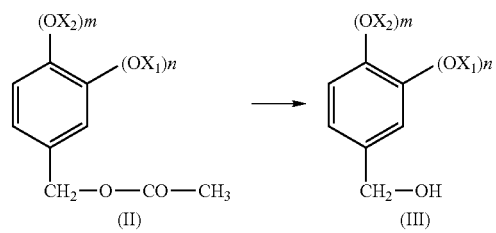

(iii) catalytic oxidation of the alcohol (III) to form the final compound (IV).

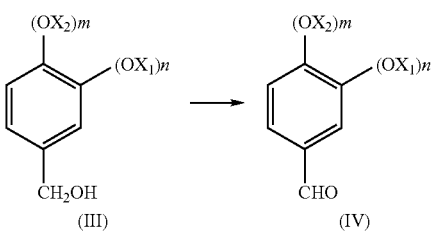

DETAILED DESCRIPTION OF THE INVENTION

In all the formulae given in the present application, $X_1$ and $X_2$, the same or different, are linear or branched C1-C8 alkyls, n and m are 0, 1 or 2, with the proviso that n and m are not simultaneously 0; or $(OX_1)n$ and $(OX_2)m$ taken together form an —O-T-O— group where T is chosen from —$CH_2$—, —$CH_2CH_2$—, —$CH_2CH_2CH_2$—, —$C(CH_3)_2$—. Preferably the substituents $X_1$ and $X_2$ are chosen from C1-C4 alkyl, or, taken together, correspond to the —O—$CH_2$—O— group; in this latter case, the structure of the final product (IV) corresponds to heliotropine; this compound is the preferred substance, synthesizable with the process of the present invention.

The chloromethyl derivative of formula (I), the starting product of the present process, is commercially available, or can be easily synthesised by known methods.

A preferred method for synthesizing the compound (I) consists of chloromethylating a compound of formula (V), where $X_1$, $X_2$, n and m have the previously given meaning: chloromethylation is carried out with aqueous formaldehyde or paraformaldehyde and hydrochloric acid in the absence or presence of an inert organic solvent; this latter method is preferred in that it gives rise to a product (I) with less impurities.

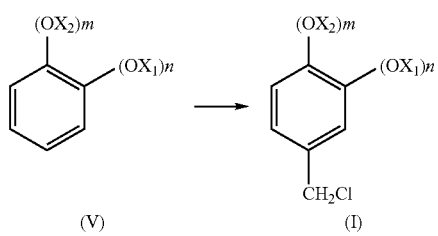

The hydrochloric acid used can be gaseous or in aqueous solution; hydrochloric acid as a 36-37% aqueous solution is preferred. The organic solvent is chosen from an aromatic, alicyclic or chlorinated solvent; toluene, cyclohexane and methylene chloride are preferred. Toluene and methylene chloride are particularly preferred. The volumes of solvent in relation to substrate (V) are between 1:1 and 1:5 (v/v); a ratio of 1:2 (v/v) is particularly preferred.

The hydrochloric acid in solution is used in quantities of between 1 and 10 equivalents in relation to the substrate, and more preferably from 2 to 4 equivalents, the best results being obtained with 3 equivalents.

The paraformaldehyde is used in quantities of between 0.5 and 2 equivalents in relation to the substrate (V), and more preferably from 0.95 to 1.25 equivalents.

The reaction temperature varies between 10° C. and 80° C., more preferably between 15° C. and 50° C., the best results being obtained between 20° C. and 25° C. Reaction times vary generally from 30 minutes to 24 hours. Considering that the selectivity of the reaction decreases over time at the expense of substrate conversion, a reaction time of between 4 and 5 hours is expedient.

At the end of the reaction, the organic phase is separated from the aqueous phase. The aqueous phase, containing essentially acid at a lower concentration and formaldehyde, can be re-used in the next cycle after re-saturating with gaseous hydrochloric acid. The organic phase, containing the chloromethylated product (I), is directly usable, as the crude product, in the subsequent aldehyde synthesis reaction.

A distinctive characteristic of the present process is the synthesis of the alcohol derivative (III) starting from the chloromethyl derivative (I) and passing via the ester intermediate (II); this synthesis pathway is a suitable alternative to directly hydrolysing the chloromethyl derivative with NaOH. In this respect, in previously conducted tests, whereby the product (I) was directly hydrolysed with NaOH, yields were obtained of the alcohol (III) which were never greater than 80%; moreover, the subsequent oxidation passage proved to be difficult due to the presence of by-products capable of inactivating the catalyst.

In the first passage (i) of the process of the present invention, formation of the ester intermediate (II) occurs by condensing the chloromethyl derivative (I) with an alkaline acetate, as in the following scheme:

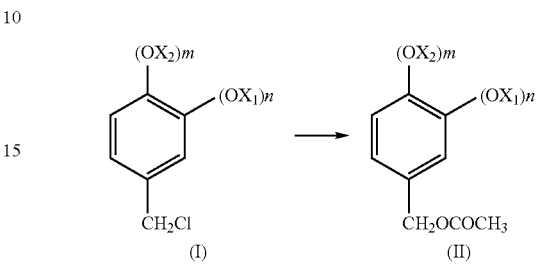

The reaction can be conducted directly in a biphasic system by dispensing the organic solution of the derivative (I) onto an aqueous solution containing an alkaline acetate, preferably sodium acetate. The volume of water used must not be less than 50% of the organic phase.

The mole ratios of acetate to chloromethyl derivate (I) can be from 1:1 to 3:1, but preferably from 1.3:1 to 1.6:1 and more preferably 1.4:1.

The reaction temperature can vary between 40° C. and 85° C., more preferably between 70° C. and 80° C.

The second passage (ii) of the process of the invention consists in hydrolysing the compound (II) to form the alcohol (III),

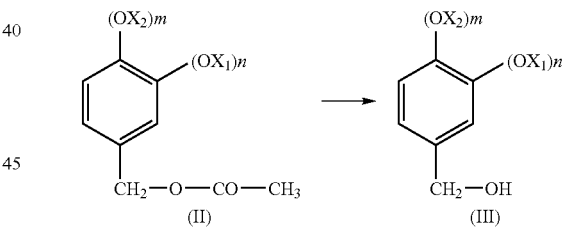

The reaction can be advantageously conducted directly in the biphasic system derived from passage (i), without the need for purification. The reaction is achieved by adding aqueous sodium hydroxide and a phase transfer catalyst of the ammonium salt group, for example hydrated tetrabutylammonium chloride, Aliquat 336 or tetrabutylammonium bromide, to the product of passage (i).

The molar ratio of NaOH to chloromethyl derivative (I) is between 3:1 and 1:1, preferably 1.5:1.

The molar ratio of phase transfer catalyst to NaOH is between 1:100 and 1:400, and preferably 1:300.

The reaction is conducted between 60° C. and 85° C., preferably at 80° C.; the ester (II) conversion is completed after about 2 hours, and the yield of alcohol (III) is between 90 and 96% in relation to the chloromethyl derivative.

The third passage (iii) of the process of the invention consists of oxidizing the compound of formula (III) to give the final compound of formula (IV).

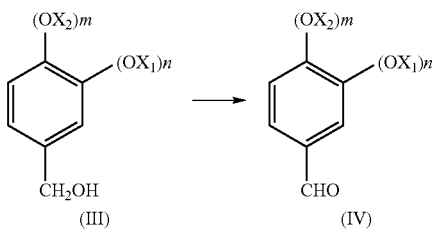

This reaction can also be favourably conducted on the crude product from the preceding reaction, without the need for intermediate purification.

Oxidation of the alcohol (III) takes place in the crude organic mixture; the weight ratio of water to organic solvent is preferably between 0.5:1 and 2:1, being preferably 1:1. The reaction takes place in the presence of a suitable oxidation catalyst, air or oxygen and an alkaline hydroxide. Air is particularly preferred. The oxidation catalysts are a family of known compounds which comprises Ru, Pd, Pt, Au alone or doped with suitable metals such as Bi, possibly supported on carbon or aluminium; other examples of catalysts are Raney Ni and Raney Ni heterogenized on hydrotalcite.

Oxidation occurs in the liquid phase using air as the oxidant. Preferred catalysts are those based on Ru and Pt supported on carbon in quantities varying between 1 and 10% (% w/w). The weight percentage of the catalyst in relation to the alcohol (III), considered as 50 wt % wetted catalyst supported on carbon, varies from 1% to 15%, preferably between 7% and 14%. The toluene/water mixture was shown to be the best solvent in terms of reaction rate and moreover the basicity of the reaction environment was found to be of fundamental importance: in this respect the reaction rate increases as pH increases, without influencing aldehyde selectivity. The quantity of base, preferably sodium hydroxide, relative to the alcohol (III), is between 0.25 and 2 equivalents, more preferably 1 equivalent.

The reaction temperature is between 20° C. and 85° C., preferably between 40° C. and 80° C. The fed air can be used as such or diluted with nitrogen; in any case the moles of oxygen fed as air or as pure oxygen, relative to the substrate (III) to be oxidized, are between 3:1 and 6:1.

The resulting crude product is purified with the usual techniques to isolate the product (IV) in the pure state.

The following non-limiting examples serve to illustrate the present invention.

Experimental Part

Synthesis of 5-carboxaldehyde benzo[1.3]dioxole (a) Synthesis of chloromethyl-benzodioxole
The following are introduced into a 2 litre flask:
82.9 g p-$CH_2O$ (96%) (2.6 moles)
300 g 1,3-benzodioxole (99.4%) (2.4 moles)
540 ml of toluene
784 g HCl (37%) (7.9 moles).
The mixture is allowed to react for 4 hours under a head of $N_2$, maintaining the temperature at 20-25° C. with an ice bath.

After separating the phases, a crude product of 818.0 g is obtained with the following composition:
1,3-benzodioxole 15.6% w/w (127.6 g) (1.05 moles)
5-chloromethyl-1,3-benzodioxole 25.94% w/w (212.19 g) (1.24 moles)
Conversion of 1,3-benzodioxole: 57.2%
Selectivity of 5-chloromethyl-1,3-benzodioxole: 89.0%
Yield of 5-chloromethyl-1,3-benzodioxole: 50.9%

(b) Synthesis of Piperonyl Acetate from 5-chloromethyl-1,3-benzodioxole 144.2 g of $CH_3COONa$ (99%) (1.7 moles) and 365 ml $H_2O$ are introduced into a 2 litre flask.

The flask is placed under agitation and the temperature of the mixture is brought to 80°-85° C. under a head of $N_2$.

The previously prepared crude product of the 5-chloromethyl-1,3-benzodioxole synthesis is fed drop-wise into the mixture over 2 hours.

The mixture is allowed to react for another 2 hours following the drop-wise addition.

(c) Synthesis of Piperonyl Alcohol by Hydrolysing Piperonyl Acetate 1.92 g of tetrabutylammonium chloride hydrate (98%) (0.00677 moles) and 76.9 g NaOH (97%) (1.9 moles) are added to the crude piperonyl acetate synthesis product of the previous synthesis, at ambient temperature.

While adding the NaOH the temperature rises to 45-50° C.
The temperature is brought to 80-85° C. under agitation and $N_2$ flow.

The mixture is allowed to react for 2 hours under these conditions. After cooling, the mixture is filtered. The phases are separated and a crude product weighing 777.9 g is obtained, with the following composition:
piperonyl alcohol 23.74% w/w (184.67 g) (1.2 moles)
1,3-benzodioxole 16.12% w/w (125.4 g) (1.03 moles)
Conversion of 5-chloromethyl-1,3-benzodioxole: 100%
Yield of piperonyl alcohol relative to 5-chloromethyl-1,3-benzodioxole: 97.6%

(d) Oxidation of the Piperonyl Alcohol/1,3-benzodioxole Mixture

The previously obtained crude piperonyl alcohol synthesis product is introduced into a 1 litre flask.

50.1 g NaOH pellets (97%) (1.21 moles) dissolved in 750 ml $H_2O$ and 24 g of 5% Pt catalyst wetted to 53.6% are added.

The temperature is brought to 80-85° C. under $N_2$ flow, after which a flow of air is supplied at about 540 ml/min measured on leaving the reaction environment.

Alcohol conversion is essentially complete after 10 hours of reaction time.

The air flow is stopped and the reaction mixture is brought to ambient temperature under $N_2$ flow. The catalyst is filtered off and the phases are then separated.

A crude product weighing 1035.45 g is obtained composed of the following:

| | |
|---|---|
| piperonyl alcohol | 0.08% w/w (0.828 g) |
| heliotropine | 14.48% w/w (150 g) |
| 1,3-benzodioxole | 11.9% w/w (123.22 g) |

Conversion of piperonyl alcohol=99.6%
Yield of heliotropine=82.3%

(e) Purification of the Crude Product and Crystallization of Heliotropine

The crude reaction product is distilled separating firstly the unreacted 1,3-benzodioxole at 40° C./1.5 mbar (121.8 g) and then the heliotropine or 5-carboxaldehyde-1,3-benzodioxole at 91° C./1.5 mbar, to obtain 145.5 g heliotropine at 95.8% (% a/a)

Heliotropine yield by distillation: 92.7%

Heliotropine thus obtained can be suitably crystallized by using an isopropanol/$H_2O$ mixture.

After drying at 30° C./23 mbar, 131 g of crystalline heliotropine is obtained with:
concentration: 99.2% (% w/w)
concentration: 99.95% (% a/a)

Crystallization yield 89.3%.

The invention claimed is:

1. Process for obtaining a compound of formula (IV)

(IV)

in which $X_1$ and $X_2$, the same or different, are linear or branched C1-C8 alkyls, n and m are 0, 1 or 2, with the proviso that n and m cannot be simultaneously 0; or $(OX_1)n$ and $(OX_2)m$ taken together form an O-T-O group where T is chosen from —$CH_2$—, —$CH_2CH_2$—, —$CH_2CH_2CH_2$—, —$C(CH_3)_2$—, said process comprising the following passages:

(i) treating a chloromethyl derivative of formula (I) with an alkaline acetate to form the acetyl derivative of formula (II), where $X_1$, $X_2$, m and n have the aforesaid meanings;

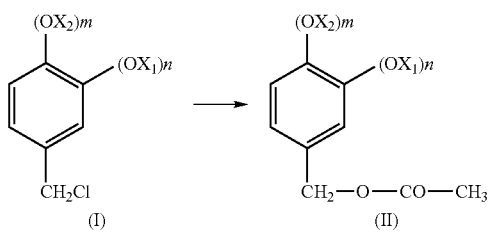

(ii) hydrolyzing compound (II) to form the alcohol (III), where $X_1$, $X_2$, m and n have the aforesaid meanings;

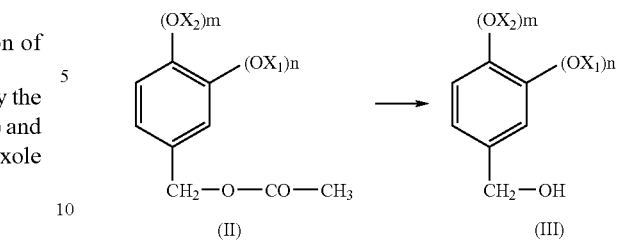

(iii) catalytic oxidation of the alcohol (III) to form the compound (IV)

wherein the passage (iii) is conducted by treating in the liquid phase the product of passage (ii) with air or oxygen and an alkaline hydroxide used in a hydroxide/alcohol (III) equivalent ratio between 1 and 2, in the presence of a suitable oxidation catalyst.

2. Process as claimed in claim 1, wherein $X_1$ and $X_2$ are chosen from a C1-C4 alkyl or taken together correspond to the —O—$CH_2$—O— group.

3. Process as claimed in claim 1, wherein the passage (i) is conducted by adding an organic solution of the derivative (I) to an aqueous solution containing an alkaline acetate such that, in the resultant mixture, the volume of water constitutes at least 50% of the organic phase.

4. Process as claimed in claim 3, wherein the molar ratios of alkaline acetate to chloromethyl derivative (I) are between 1:1 and 3:1 and the reaction temperature is between 40° C. and 85° C.

5. Process as claimed in claim 4, wherein the molar ratios of alkaline acetate to chloromethyl derivative (I) are between 1.3:1 and 1.6:1 and the reaction temperature is between 70° C. and 80° C.

6. Process as claimed in claim 1, wherein the passage (ii) is conducted by adding aqueous NaOH and a phase transfer catalyst, of the ammonium salts group, to the product of passage (i).

7. Process as claimed in claim 6, wherein the molar ratio of NaOH to chloromethyl derivative (I) is between 3:1 and 1:1 and that of the phase transfer catalyst to NaOH is between 1:100 and 1:400, the reaction being conducted at a temperature between 60° C. and 85° C.

8. Process as claimed in claim 1, wherein the passage (iii) is conducted in a water: organic solvent mixture, in which the weight ratio of water to organic solvent present is between 0.5:1 and 2:1.

9. Process as claimed in claim 1, wherein in passage (iii) the weight percentage of the catalyst, considered as 50 wt % wetted relative to the alcohol (III) varies from 1% to 15%, the reaction solvent is a toluene/water mixture, the quantity of base is between 1 and 2 equivalents relative to the alcohol (III), the reaction temperature is between 20° C. and 85° C., and the moles of fed oxygen are 3-6 times in excess of the substrate to be oxidized.

* * * * *